United States Patent [19]

Ali et al.

[11] 4,244,865
[45] Jan. 13, 1981

[54] α HYDROXY TRIPEPTIDE SUBSTRATES

[75] Inventors: Akhtar Ali, Vernon Hills; Robert G. Hiltibran, Gurnee, both of Ill.

[73] Assignee: Abbott Laboratories, North Chicago, Ill.

[21] Appl. No.: 99,376

[22] Filed: Dec. 3, 1979

[51] Int. Cl.³ .................. C07C 103/52; C07G 7/00
[52] U.S. Cl. .......................... 260/112.5 R; 435/4; 435/14
[58] Field of Search .............. 260/112.5 R; 435/4, 435/14

[56] References Cited

U.S. PATENT DOCUMENTS

| | | | |
|---|---|---|---|
| 4,028,318 | 6/1977 | Aurell et al. | 260/112.5 R |
| 4,061,625 | 12/1977 | Ekenstam et al. | 260/112.5 R |
| 4,070,245 | 1/1978 | Svendsen | 260/112.5 R |
| 4,137,225 | 1/1979 | Ekenstam et al. | 260/112.5 R |

Primary Examiner—Delbert R. Phillips
Assistant Examiner—Blondel Hazel
Attorney, Agent, or Firm—Neal O. Willmann

[57] ABSTRACT

This invention relates to the synthesis and use of novel α hydroxy tripeptide substrates which are useful in the quantitative determination of proteolytic enzymes such as thrombin and trypsin. In use, the disclosed substrates are hydrolyzed by a proteolytic enzyme to yield a moiety that can be evaluated spectrophotometrically to indicate the quantity of enzyme present.

8 Claims, No Drawings

α HYDROXY TRIPEPTIDE SUBSTRATES

BACKGROUND OF THE INVENTION

The novel substrates are useful as reagents in the detection and determination of proteolytic enzymes which cleave amide linkages in peptide chains on the carboxyl side of arginine and lysine residues.

Structurally related chromogenic and fluorometric substrates have been described in U.S. Pat. Nos. 3,886,136; 4,028,318; 4,061,625 and 4,070,245; however, none of these substrates benefit from substituting an α hydroxide for an α-amino group in the terminal moiety.

Specifically, it has been found that when an analogous α hydroxy acid is substituted at the N terminous or $P^3$ site of a tripeptide substrate at least three advantages are realized. Most notably, solubility in aqueous buffers is greater with the α hydroxy than with benzoyl blocked amino acid substrates. In addition, the α hydroxy substrates show no susceptibility to amino peptidase activity thereby eliminating the need for blocking groups on the N terminous and obviating the use of the D form over the L form (natural) of the N terminous amino acid. The α hydroxy analogs also simplify synthesis by eliminating the need to block and deblock the hydroxy substituent during synthesis. The α hydroxy substrates also show similar enzymatic reactivities with kinetics very similar to their α amino acid counterparts.

SUMMARY OF THE INVENTION

In particular, this invention relates to novel spectrophotometrically detectable substrates that can be characterized as α hydroxy tripeptides of the following formula:

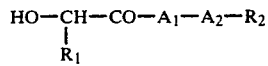

Wherein
  $R_1$ is selected from the group consisting of hydrogen, lower alkyl ($C_1$-$C_4$) straight chain or branched and benzyl;
  $R_2$ is selected from the group consisting of paranitroanilide, nitrophenyl, methyl nitrophenyl, dinitrophenyl, naphthyl, nitronapthyly, 4-methyl-7-coumarylamide, 1-methoxy-3-naphthylamide and thio benzyl ester;
  $A_1$ is selected from the group of L amino acids consisting of glycine, alanine, valine, leucine, proline, isoleucine, serine, threonine, aspartic acid, asparagine, glutamic acid, glutamine, lysine, hydroglycine, histidine, arginine, phenylalanine, tyrosine, tryptophan, cysteine, methionine, pipercolic; and
  $A_2$ is either L-arginine or L-lysine.

A more preferred group of substrates includes those of the formula:

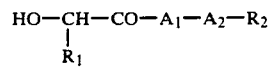

Wherein
  $R_1$ is selected from the group consisting of hydrogen, lower alkyl ($C_1$-$C_4$) straight chain or branched and benzyl;
  $R_2$ is selected from the group consisting of paranitroanilide, nitrophenyl, thio benzyl ester;
  $A_1$ is selected from the group of L amino acids consisting of glycine, alanine, valine, proline, isoleucine, aspartic acid, glutamic acid, and phenylalanine; and
  $A_2$ is either L-arginine or L-lysine.

DESCRIPTION OF THE PREFERRED EMBODIMENT

The α-hydroxy acids employed in the preparation of the claimed substrates can all be prepared according to the method described by M. Winitz, et al, J. Am.Chem. Soc., 78, 2423, (1956). Given α-hydroxy β-phenyl propionic acid and α-hydroxyisocaproic acid, the claimed substrates can be synthesized according to the following basic stepwise coupling procedure:

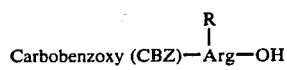

is coupled to p-nitrophenyl-isocyanate to give

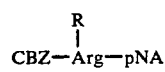

which, in turn, is treated with HBr/acetic acid to yield

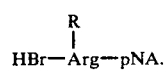

CBZ-Pro-succinimidyl ester is coupled to

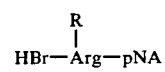

to give the protected

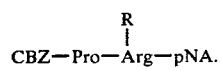

The protected dipeptide is treated with HBr/acetic acid to give

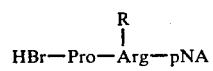

which is further coupled to an α-hydroxy acid using 1-hydroxybenzotriazole and dicyclohexylcarbodiimide. The

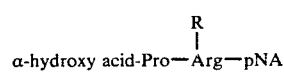

may be further reacted with HF or methanesulfonic acid to remove the guanidine-protecting R group from arginine.

Suitable R groups include methoxybenzenesulfonyl, nitro and tosyl.

The CBZ group for the α-amino protection of amino acids can be replaced by other moieties such as t-butyloxycarbonyl and O-nitrophenyl sulfonyl.

Other amino acids can be substituted successfully for those mentioned in the foregoing preparation scheme. For example, the amino acid attached directly to the detectable leaving group can be either arginine or lysine. The amino acid in the center of the tripepetide moiety can be any of the amino acids previously identified as $A_1$.

The N terminous α-hydroxy substituent, while usually prepared by substituting α-hydroxy for the analogous amine in glycine, alanine and phenylalanine, can also be derived from valine, leucine, isoleucine, serine, threonine, aspartic acid, asparagine glutamic acid, glutamine, lysine, hydroxylsine, histidine, arginine, tyrosine, tryptophan, cysteine and methionine.

A preferred chromophore is paranitroanilide but other art recognized chromic moieties such as methyl nitrophenyl, nitrophenyl, dinitrophenyl, naphthyl and nitronaphthyl may also be used. See Plapinger, et al., J. Organic Chem., 30, 1781, (1965).

Fluorometric leaving groups, well established in the art such as 4-methyl-7-coumarylamide (Morika, et al, J. Biochem., 82, 1495, (1977)); 1-methoxy-3-naphthylamide (Elarin, et al, Anal. Biochem., 80, 355, (1977)); and thio benzyl ester can also be employed.

Specific examples demonstrating the preparation of a preferred α-hydroxy substrate is set forth below:

EXAMPLE 1

Preparation of N$^\omega$-Methoxybenzenesulfonyl-L-Arginyl-p-Nitroanalide.HBr

Twenty-three grams of N$^\alpha$-carbobenzoxy-N$^\omega$-(4-methoxybenzenesulfonyl)-L-arginine, prepared according to the method described by Nishimura, et al., Chem. Pharm. Bull., 24, 1568 (1976) was dissolved in 100 ml of hexamethyl phosphoramide.

To the resulting solution was added 6.7 ml of triethylamine and 15.8 g of p-nitrophenyl isocyanate. The solution was stirred at room temperature overnight and then poured into 1300 ml of 5% sodium bicarbonate. The resulting precipitate was collected by a filtration funnel and washed separately with (2×400 ml) 5% sodium bicarbonate, (1×300 ml) water, (3×300 ml) 1 N hydrochloric acid and then (2×200 ml) water. The precipitate was dried in the filtration funnel by vacuum suction and then extracted with (3×300 ml) boiling methanol. The methanol extracts were combined and the methanol was evaporated in vacuo at 35° C. The semisolid residue was purified further by a silica gel column using 1-5% methanol in chloroform as eluent. This provided N$^\alpha$-carbobenzoxy-N$^\omega$-(4-methoxybenzenesulfonyl)-L-arginine-p-nitroanilide. 6.0 g of this material was dissolved in 30% hydrobromic acid in acetic acid. The resulting reaction mixture was kept at room temperature for 45 minutes and then poured into 400 ml of dry ether. The precipitated salt was filtered and washed with (2×100 ml) of dry ether to provide N$^\omega$-methoxybenzesulfonyl-L-arginyl-p-nitroanilide hydrobromide.

EXAMPLE 2

Preparation of N$^\alpha$-CBZ-Pro-N$^\omega$-MBS-Arg-pNA

Carbobenzoxy-L-proline-succinimidyl ester (0.7 g; 2 mMole) and N$^\omega$-MBS-L-Arg-pNA-HBr (1.1 g; 2 mMole) were dissolved in tetrahydrofuran (10 ml) and dimethylformamide (2 ml). To the reaction mixture was added n-methylmorpholine (0.24 ml; 2 mMole) and stirred at room temperature overnight. The reaction mixture was evaporated in vacuo and the oily residue was suspended in 300 ml of methylene chloride. The solution was washed with 1 N-hydrochloric acid (1×60 ml) brine solution (1×60 ml), sodium bicarbonate (saturated) solution (1×60 ml), brine solution (1×60 ml) respectively. The solution was dried over MgSO$_4$ anhydrous and concentrated to 2-3 ml. To this solution was added ether anhydrous and the precipitated product was collected by filtration. Yield=0.64 g.

EXAMPLE 3

Preparation of L-Pro-N$^\omega$-MBS-Arg-pNA.Hbr

N$^\alpha$-CBZ-L-Pro-N$^\omega$-MBS-Arg-pNA (0.64 g) was dissolved in 30% HBr/acetic acid (10 ml). The solution was kept at room temperature for one hour and then poured into anhydrous ether (50-60 ml). The precipitated product was collected by filtration and dried in a vacuum desiccator. Yield=0.45 g.

EXAMPLE 4

Preparation of α-Hydroxyacid-Pro-N$^\omega$-MBS-Arg-pNA

Pro-N$^\omega$-MBS-Arg-pNA.HBr (437 mg, 0.68 mMole), α-hydroxy acid (0.68 mMole) and 1-hydroxybenzotriazole (92 mg, 0.68 mMole) were dissolved in tetrahydrofuran (10 ml)-dimethylformamide (2 ml). The solution was cooled to 0° C. and stirred magnetically, while 0.68 mMole n-methylmorpholine (0.1 ml) and dicyclohexylcarbodiimide (140 mg, 0.68 mMole) were added. The reaction mixture was warmed to room temperature and stirred overnight. The dicyclohexylurea was filtered, and the filtrate was evaporated under vacuo. The residue was suspended or dissolved in chloroform or methanol and precipitated with ether. The solid was collected by filtration.

Following this procedure, blocked compounds listed below were also synthesized:
(1) L-α-hydroxy-β-phenylpropionic-L-Pro-N$^\omega$-MBS-L-Arg-pNA
(2) D-α-hydroxy-β-phenylpropionic-L-Pro-N$^\omega$-MBS-L-Arg-pNA
(3) L-α-hydroxyisocaproic-L-Pro-N$^\omega$-MBS-L-Arg-pNA
(4) D-α-hydroxyisocaproic-L-Pro-N$^\omega$-MBS-L-Arg-pNA
(5) Glycolic-L-Pro-N$^\omega$-MBS-L-Arg-pNA

EXAMPLE 5

α-Hydroxyacid-L-Pro-L-Arg-pNA

α-Hydroxyacid-L-Pro-L-N$^\omega$-MBS-Arg-pNA (0.5 mMole) was dissolved in methane sulfonic acid (35 sq). After 30 minutes at room temperature, the reaction mixture was poured into anhydrous ether. The precipitated product was collected by filtration. The product was further precipitated from methanol-ether and tetrahydrofuran-ether. The TLC developed with n-butanol:acetic acid:water—4:1:1 showed a single spot.

Following this procedure, the following compounds were synthesized and used as enzyme substrates:
(1) L-α-Hydroxy-β-phenylpropionic-L-Pro-L-Arg-pNA
(2) D-α-Hydroxy-β-phenylpropionic-L-Pro-L-Arg-pNA
(3) L-α-Hydroxyisocaprioc-L-Pro-L-Arg-pNA
(4) D-α-Hydroxyisocaproic-L-Pro-L-Arg-pNA
(5) Glycolic-L-Pro-L-Arg-pNA Clinically, the claimed substrates can be used to measure antithrombin III (AT III).

Antithrombin III is the major component of the human anticoagulation system. It inhibits a variety of serine proteases by forming a 1:1 complex with serine, the active center of such enzymes. The presence of heparin increases the rate of reaction at AT III with such Proteases approximately 100 fold.

The chemistry of AT III is described in the following equations:

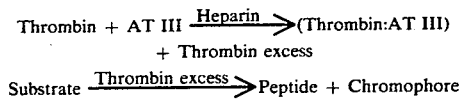
+ Thrombin excess

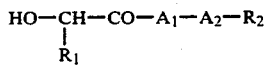

Since the presence of heparin potentiates the activity of AT III, it is possible to delineate the inhibition due to AT III from that of other plasma proteins which can also inhibit thrombin. Thus, one measures total AT III activity as an entity distinct from the "progressive antithrombin activity" which is measured in the absence of heparin. As a result, one can clearly identify a defect in the anticoagulation system as one associated with AT III rather than other protein inhibiting mechanism.

This test relies on the fact that human AT III in a specimen inhibits human α-thrombin in a 1:1 molar ratio. Excess thrombin is free to hydrolyze a colorless substrate. When this substrate is cleaved, it releases a spectrophotometrically detectable leaving group which causes a dramatic shift in the absorbance spectrum shown by the development of a detectable color or fluorescence. This cleavage of the substrate is analogous to the clevage of the arginyl-glycine bond in fibrinogen which results in the formation of fibrin. By monitoring the fluorescence color development of the reaction mixture, one can follow the course of the turnover of substrate by thrombin. Since the amount of AT III and the amount of fluorescence or color produced are inversely proportional, the level of AT III can readily be determined.

We claim:

1. A chromogenic substrate for the quantitative determination of proteolytic enzymes which split peptide bonds on the carboxyl side of arginine and lysine of the formula:

$$HO-CH(R_1)-CO-A_1-A_2-R_2$$

wherein $R_1$ is selected from the group consisting of hydrogen, lower alkyl ($C_1$–$C_4$) straight chain or branched and benzyl; $R_2$ is selected from the group consisting of paranitroanilide, nitrophenyl, methylnitrophenyl, dinitrophenyl, naphthyl and nitronaphthyl; $A_1$ is selected from the group of L amino acids consisting of glycine, alanine, valine, leucine, proline, isoleucine, serine, threonine, aspartic acid, asparagine, glutamic acid, glutamine, lysine, hydroglycine, histidine, arginine, phenylalanine, tyrosine, tryptophan, cysteine, pipercolic acid and methionine; and $A_2$ is either L-arginine or L-lysine.

2. A chromogenic substrate for the quantitative determination of proteolytic enzymes which split peptide bonds on the carboxyl side of arginine and lysine of the formula:

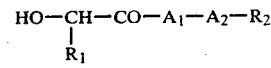

wherein $R_1$ is selected from the group consisting of hydrogen, lower alkyl ($C_1$–$C_4$) straight chain or branched and benzyl; $R_2$ is selected from the group consisting of paranitroanilide, nitrophenyl, methylnitrophenyl, dinitrophenyl, naphthyl and nitronaphthyl; $A_1$ is selected from the group of L-amino acids consisting of glycine, alanine, valine, leucine, proline, isoleucine, threonine, aspartic acid, asparagine, glutamic acid, phenylalanine and methionine; and $A_2$ is either L-arginine or L-lysine.

3. A chromogenic substrate for the quantitative determination of proteolytic enzymes which split peptide bonds on the carboxyl side of arginine and lysine of the formula:

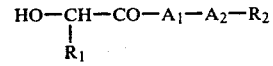

wherein $R_1$ is selected from the group consisting of hydrogen, lower alkyl ($C_1$–$C_4$) straight chain or branched and benzyl; $R_2$ is selected from the group consisting of paranitroanilide and nitrophenyl; $A_1$ is selected from the group of L amino acids consisting of glycine, alanine, valine, proline, isoleucine, aspartic acid, glutamic acid and phenylalanine; and $A_2$ is either L-arginine or L-lysine.

4. The chromogenic substrate according to claim 3 glycolic-L-prolyl-L-arginyl-p-nitroanilide.

5. The chromogenic substrate according to claim 3 L-α-hydroxyisocaproic-L-prolyl-L-arginyl-p-nitroanilide.

6. The chromogenic substrate according to claim 3 D-α-hydroxyisocaproic-L-prolyl-L-arginyl-p-nitroanilide.

7. The chromogenic substrate according to claim 3 L-α-hydroxy-β-phenylpropionic-L-prolyl-L-arginyl-p-nitroanilide.

8. The chromogenic substrate according to claim 3 D-α-hydroxy-β-phenylpropionic-L-prolyl-L-arginyl-p-nitroanilide.

* * * * *